US00PP21868P2

(12) United States Plant Patent
Geibel

(10) Patent No.: US PP21,868 P2
(45) Date of Patent: Apr. 12, 2011

(54) GERANIUM PLANT NAMED 'PACRUBY'

(50) Latin Name: *Pelargonium peltatum*
Varietal Denomination: Pacruby

(75) Inventor: Martin Geibel, Dresden (DE)

(73) Assignee: Elsner PAC Jungpflanzen GbR, Dresden (DE)

( * ) Notice: Subject to any disclaimer, the term of this patent is extended or adjusted under 35 U.S.C. 154(b) by 0 days.

(21) Appl. No.: 12/655,760

(22) Filed: Jan. 6, 2010

(51) Int. Cl.
*A01H 5/00* (2006.01)

(52) U.S. Cl. ..... Plt./332

(58) Field of Classification Search ..... Plt./332, Plt./330, 324
See application file for complete search history.

*Primary Examiner* — Annette H Para
(74) *Attorney, Agent, or Firm* — C. A. Whealy

(57) ABSTRACT

A new and distinct cultivar of Ivy Geranium plant named 'Pacruby', characterized by its outwardly spreading to trailing and cascading plant habit; vigorous growth habit; freely branching habit; dark green-colored leaves; freely flowering habit; semi-double-type deep red-colored flowers; and relatively good garden performance.

1 Drawing Sheet

Botanical designation: *Pelargonium peltatum.*
Cultivar denomination: 'PACRUBY'.

BACKGROUND OF THE INVENTION

The present invention relates to a new and distinct cultivar of Ivy Geranium plant, botanically known as *Pelargonium peltatum*, and hereinafter referred to by the name 'Pacruby'.

The new Ivy Geranium plant is a product of a planned breeding program conducted by the Inventor in Dresden, Germany. The objective of the breeding program is to create new freely flowering Ivy Geranium plants with uniform plant habit and attractive flower coloration.

The new Ivy Geranium plant originated from a cross-pollination made by the Inventor in Dresden, Germany during the summer of 2005 of two unnamed proprietary selections of *Pelargonium peltatum*, not patented. The new Ivy Geranium plant was discovered and selected by the Inventor as a flowering plant from within the progeny of the stated cross-pollination in a controlled greenhouse environment in Dresden, Germany in June, 2006.

Asexual reproduction of the new Ivy Geranium plant by vegetative terminal cuttings in a controlled greenhouse environment in Dresden, Germany since December, 2006, has shown that the unique features of this new Ivy Geranium plant are stable and reproduced true to type in successive generations.

SUMMARY OF THE INVENTION

Plants of the new Ivy Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacruby'. These characteristics in combination distinguish 'Pacruby' as a new and distinct cultivar of Ivy Geranium:

1. Outwardly spreading to trailing and cascading plant habit.
2. Vigorous growth habit.
3. Freely branching habit.

4. Dark green-colored leaves.
5. Freely flowering habit.
6. Semi-double-type deep red-colored flowers.
7. Relatively good garden performance.

Plants of the new Ivy Geranium differ primarily from plants of the parent selections in plant vigor, plant uniformity and flower color.

Plants of the new Ivy Geranium can be compared to plants of the *Pelargonium peltatum* 'Pengra', disclosed in U.S. Plant Pat. No. 14,112. In side-by-side comparisons conducted in Dresden, Germany, plants of the new Ivy Geranium differed from plants of 'Pengra' in the following characteristics:

1. Plants of the new Ivy Geranium were more freely branching than plants of 'Pengra'.
2. Leaves of plants of the new Ivy Geranium were glossier and had more undulate margins than leaves of plants of 'Pengra'.
3. Plants of the new Ivy Geranium and 'Pengra' differed in flower color.

BRIEF DESCRIPTION OF THE PHOTOGRAPH

The accompanying colored photograph illustrates the overall appearance of the new Ivy Geranium plant, showing the colors as true as it is reasonably possible to obtain in colored reproductions of this type. Colors in the photograph may differ slightly from the color values cited in the detailed botanical description which accurately describe the colors of the new Ivy Geranium plant.

The photograph comprises a side perspective view of a typical flowering plant of 'Pacruby' grown in a container.

DETAILED BOTANICAL DESCRIPTION

The aforementioned photograph and following observations, measurements and values describe plants grown in 19-cm containers in Dresden, Germany in a glass-covered greenhouse during the summer under conditions which closely approximate commercial Ivy Geranium production. During the production of the plants, day temperatures ranged from 18° C. to 20° C., night temperatures averaged 18° C. and light levels ranged from 15 kilolux to 100 kilolux. Plants were pinched twice and were seven months old when the photograph was taken and were nine months old when the description was taken. In the detailed description, color references are made to The Royal Horticultural Society Colour Chart, 1995 Edition, except where general terms of ordinary dictionary significance are used.

Botanical classification: *Pelargonium peltatum* 'Pacruby'.

Parentage:

*Female, or seed, parent.*—Unnamed proprietary selection of *Pelargonium peltatum*, not patented.

*Male or pollen parent.*—Unnamed proprietary selection of *Pelargonium peltatum*, not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer and winter.*—About four weeks at temperatures of 20° C.

*Root description.*—Fine, fibrous; white in color.

*Rooting habit.*—Freely branching; dense.

Plant description:

*Plant and growth habit.*—Outwardly spreading to trailing and cascading plant habit; vigorous growth habit; rapid growth rate.

*Branching habit.*—Freely basal branching habit with about 22 lateral branches developing per plant.

*Plant height, to top of umbels.*—About 30 cm.

*Plant height, to top of leaves.*—About 25 cm.

*Plant width.*—About 50 cm.

*Lateral branches.*—Length: About 30 cm to 60 cm. Diameter: About 4 mm. Internode length: About 2 cm to 4 cm. Texture: Slightly pubescent. Color: Close to 144A.

Foliage description:

*Arrangement.*—Alternate or mostly opposite; simple.

*Length.*—About 3.5 cm.

*Width: About* 5.5 cm.

*Shape.*—Ivy-shaped, lobed.

*Apex.*—Acute.

*Base.*—Cordate.

*Margin.*—Entire with lobes; undulate.

*Venation pattern.*—Palmate.

*Texture, upper and lower surfaces.*—Slightly pubescent; leathery.

*Color.*—Developing and fully expanded leaves, upper surface: Close to 137A; venation, close to 144A. Developing and fully expanded leaves, lower surface: Close to 137C; venation, close to 144A. Zonation pattern: Location from margin: About 2 cm. Width: About 3 mm. Color: Close to 200C. Petiole: Length: About 3.5 cm. Diameter: About 2 mm. Texture, upper and lower surfaces: Pubescent; slightly rough. Color, upper and lower surfaces: Close to 137C.

Flower description:

*Flower arrangement.*—Semi-double-type rounded flowers arranged in hemispherical umbels; umbels arising from apical leaf axils and displayed above the foliage on strong peduncles; flowers face upright to outward depending on position in umbel.

*Fragrance.*—None detected.

*Quantity of flowers.*—Freely flowering habit; numerous umbels develop per plant, each umbel with about six open flowers.

*Flowering season.*—Plants begin flowering about 105 days after planting; in the garden in Dresden, Germany, plants flower continuously from May until frost in the autumn.

*Flower longevity.*—Individual flowers last about six to ten days on the plant; umbels last about three to four weeks on the plant; flowers persistent.

*Umbel height.*—About 7 cm.

*Umbel diameter.*—About 10 cm.

*Flower diameter.*—About 5 cm.

*Flower depth* (*height*).—About 2 cm.

*Flower buds.*—Length: About 1 cm. Diameter: About 5 mm. Shape: Roughly spindle-shaped. Color: Close to 144A.

*Petals.*—Quantity per flower: About five. Length: About 2.6 cm. Width: About 1.7 cm. Shape: Obovate. Apex: Rounded. Base: Attenuate. Margin: Entire; undulate. Texture, upper and lower surfaces: Smooth, glabrous; velvety. Color: When opening and fully opened, upper surface: Close to 45A; towards the base, close to 155D; venation, close to 45A. When opening and fully opened, lower surface: Close to 50A; towards the base, close to 155D; venation, close to 50A.

*Petaloids.*—Quantity per flower: About eight to eleven. Length: About 1.5 cm to 2 cm. Width: About 5 mm to 10 mm. Shape: Irregular. Apex: Rounded. Base: Attenuate. Margin: Entire. Texture, upper and lower surfaces: Rugose, glabrous; velvety. Color: When opening and fully opened, upper surface: Close to 45A; towards the base, close to 155D; venation, close to 45A. When opening and fully opened, lower surface: Close to 50A; towards the base, close to 155D; venation, close to 50A.

*Sepals.*—Quantity per flower: About five. Length: About 1.3 cm. Width: About 3 mm. Shape: Lanceolate. Apex: Acute. Margin: Entire. Texture, upper and lower surfaces: Slightly pubescent. Color, upper and lower surfaces: Close to 144A.

*Peduncle* (*umbel stem*).—Length: About 14 cm. Diameter: About 3 mm. Strength: Strong, flexible. Angle: Erect to outwardly spreading. Texture: Slightly pubescent. Color: Close to 144A.

*Pedicel* (*individual flower stem*).—Length: About 2.5 cm. Diameter: About 2 mm. Strength: Strong; flexible. Texture: Slightly pubescent. Color: Close to 144A.

*Reproductive organs.*—Androecium: Stamen quantity per flower: About 10 to 15. Anther length: About 2 mm. Anther shape: Tubular. Anther color: Close to 200A. Pollen amount: Scarce. Pollen color: Close to 163C. Gynoecium: Pistil quantity per flower: One. Pistil length: About 1 cm. Stigma shape: Five to six-parted. Stigma color: Purple. Style length: About 3 mm. Style color: Close to 155D. Ovary color: Close to 148B.

*Seeds/fruits.*—Seed and fruit development have not been observed on plants of the new Ivy Geranium.

Disease/pest resistance: Plants of the new Ivy Geranium have not been observed to be resistant to pathogens and pests common to Ivy Geraniums.

Garden performance: Plants of the new Ivy Geranium have been observed to tolerate rain, wind and temperatures ranging from about 1° C. to about 35° C. to 40° C. and have demonstrated relatively good garden performance.

It is claimed:

1. A new and distinct Ivy Geranium plant named 'Pacruby' as illustrated and described.

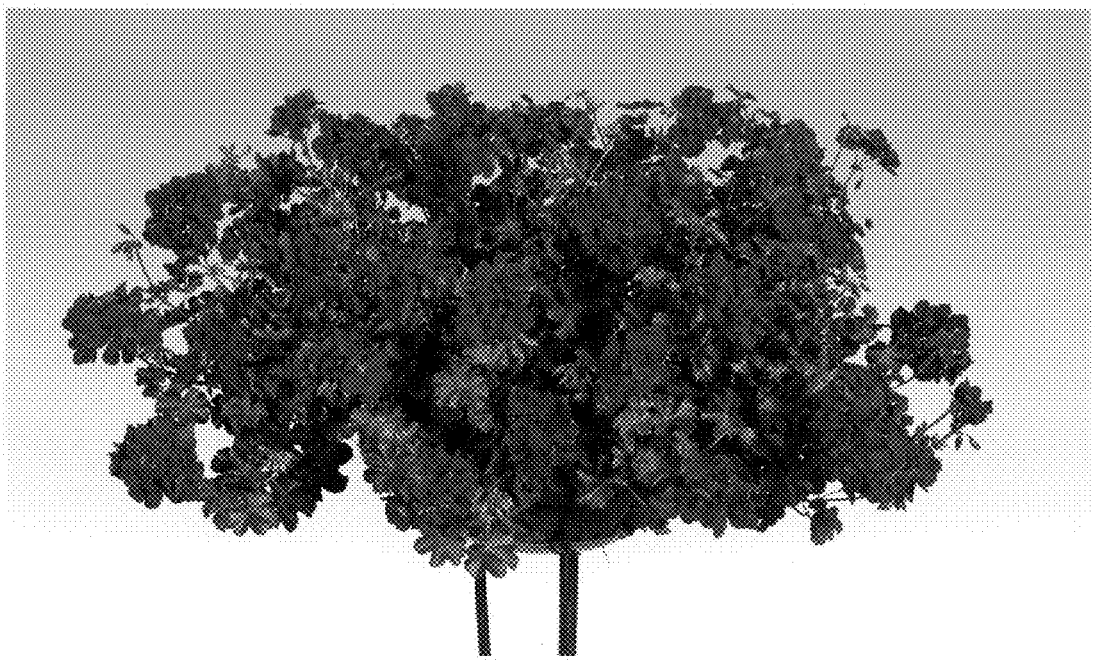

* * * * *